(12) United States Patent
Klessig et al.

(10) Patent No.: US 7,592,504 B2
(45) Date of Patent: Sep. 22, 2009

(54) METHODS FOR DETERMINING SPECIFICITY OF RNA SILENCING AND FOR GENETIC ANALYSIS OF THE SILENCED GENE OR PROTEIN

(75) Inventors: Daniel F. Klessig, Dryden, NY (US); Dhirendra Kumar, Jonesborough, TN (US)

(73) Assignee: Boyce Thompson Istitute for Plant Research, Inc., Ithaca, NY (US)

( * ) Notice: Subject to any disclaimer, the term of this patent is extended or adjusted under 35 U.S.C. 154(b) by 277 days.

(21) Appl. No.: 11/452,821

(22) Filed: Jun. 14, 2006

(65) Prior Publication Data

US 2006/0287272 A1    Dec. 21, 2006

Related U.S. Application Data

(60) Provisional application No. 60/691,413, filed on Jun. 17, 2005.

(51) Int. Cl.
*C12N 15/82* (2006.01)
*C12N 15/00* (2006.01)

(52) U.S. Cl. ..................... 800/285; 435/455

(58) Field of Classification Search ................ None
See application file for complete search history.

(56) References Cited

FOREIGN PATENT DOCUMENTS

WO    WO 9746690 A1  * 12/1997

OTHER PUBLICATIONS

Chuang et al., PNAS, 2000, vol. 97, pp. 4985-4990.*
Saxena, S., et al., "Small RNAs with imperfect match to endogenous mRNA repress translation," J. Biol. Chem., 278 (45):44312-44319, (2003).
Kumar, D., et al., "High-affinity salicylic acid-binding protein 2 is required for plant innate immunity and has salicylic acid-stimulated lipase activity," PNAS, 100(26):16101-16106, (Dec. 23, 2003).
Couzin, J., "RNAi shows cracks in its armor," Science, 306:1124-1125, (Nov. 12, 2004).
Jackson, A.L., et al., "Noise amidst the silence: off-target effects of siRNAs?" Trends in Genetics, 20(11):521-524, (Nov. 2004).
Jackson, A.L., et al., "Expression profiling reveals off-target gene regulation by RNAi," Nature Biotechnology, 21 (6):635-637 and one erratum sheet, (Jun. 2003).
Scacheri, P.C., et al., "Short interfering RNAs can induce unexpected and divergent changes in the levels of untargeted proteins in mammalian cells," PNAS, 101(7):1892-1897 and one sheet of abstract, (Feb. 17, 2004).
Bridge, A.J., et al., "Induction of an interferon response by RNAi vectors in mammalian cells," Nature Genetics, 34 (3):263-264 (Jul. 2003).
Gustafsson, C., et al., "Codon bias and heterologous protein expression," Trends in Biotechnology, 22 (7):346-353, (Jul. 2004).
Kamath, R.S., et al., "Systematic functional analysis of the *Caenorhabditis elegans* genome using RNAi," Nature, 421:231-237, (Jan. 16, 2003).
Raoul, C., et al., "Lentiviral-mediated silencing of SOD1 through RNA interference retards disease onset and progression in a mouse model of ALS," Nature Medicine, 11(4):423-428, (Apr. 2005).
Xia, H., et al., "RNAi suppresses polyglutamine-induced neurodegeneration in a model of spinocerebellar ataxia," Nature Medicine, 10(8):816-820, (Aug. 2004).
Ralph, G.S., et al., "Silencing mutant SOD1 using RNAi protects against neurodegeneration and extends survival in an ALS model," Nature Medicine, 11(4):429-433, (Apr. 2005).
Shankar, P., et al., "The prospect of silencing disease using RNA interference," JAMA, 293(11):1367-1373, (Mar. 16, 2005).
Adams, A., "RNAi inches toward the clinic as genome-wide research efforts continue, drug developers eye possible therapeutic approaches," The Scientist, 18(6):32, 12 sheets, (Mar. 29, 2004).

* cited by examiner

*Primary Examiner*—Ashwin Mehta
(74) *Attorney, Agent, or Firm*—Dann, Dorfman, Herrell & Skillman; Kathleen D. Rigaut

(57) ABSTRACT

Methods and kits for determining the specificity of siRNAs for their targets are provided. Also provided is a method for performing genetic analysis of the target protein or gene using different versions of a synthetic gene to complement the phenotype induced by RNAi-mediated silencing of the target protein and/or gene of interest. Finally, a method for treating genetic disorders associated with production of mutated proteins is also disclosed.

13 Claims, 4 Drawing Sheets

|  #C3 | silenced #1 | | |
| :---: | :---: | :---: | :---: |
| empty vector | empty vector | nat SABP2 | syn SABP2 |
|  |  |  |  |
| 1° 1.85±0.09 | 1.99±0.07 | 1.85±0.14 | 1.78±0.18 |
| 2° 0.92±0.12 | 1.48±0.20 | 1.58±0.21 | 0.87±0.21 |
| SAR + | − | − | + |

METHODS FOR DETERMINING SPECIFICITY OF RNA SILENCING AND FOR GENETIC ANALYSIS OF THE SILENCED GENE OR PROTEIN

This application claims priority under 35 U.S.C. §119(e) to U.S. Provisional Patent Application No. 60/691,413, filed on Jun. 17, 2005. The foregoing application is incorporated by reference herein.

Pursuant to 35 U.S.C. §202(c), it is acknowledged that the U.S. Government has certain rights in the invention described herein, which was made in part with funds from the National Science Foundation, Grant No. IBN-0241531.

FIELD OF THE INVENTION

The present invention relates to the fields of molecular biology, genetics and regulation of gene expression. More specifically the invention relates to methods for assessing the specificity of RNA silencing in plants and other organisms and for genetic analysis of the silenced gene or protein. Method are also provided for complementing genetic defects using synthetic nucleic acid constructs encoding wild type proteins which are not subject to RNAi.

BACKGROUND OF THE INVENTION

Several publications and patent documents are cited throughout this application in order to more fully describe the state of the art to which this invention pertains. Each of these citations is incorporated by reference herein.

RNA interference (RNAi) relates to a mechanism of selective gene silencing mediated through short interfering RNA (siRNA) and may be a general feature of gene regulation and expression in most, if not all, eukaryotes. RNAi technology has made pan-genomic functional gene analysis a reality and is a powerful strategy to quickly identify and validate new targets for therapeutic invention. In 2002, Science named RNAi Breakthrough of the Year, while Fortune in 2003 proclaimed it biotech's next billion dollar breakthrough. Despite the early success of RNAi, recent reports suggest that siRNAs are not always as specific as was first assumed (1,2). The siRNA silencing of non-targeted genes, termed off-target effects (OTE), often appear to be caused by silencing target gene homologs and/or other genes that share partial sequence complementarity to the siRNA (3). Since some base pair mismatches are tolerated in this type of OTE, it is thought that the siRNA functions as a micro RNA (miRNA) and represses translation of transcripts with partial homology (4,5). This type of OTE decreases protein, but not necessarily mRNA, concentration of the non-targeted gene. Unfortunately, the lack of siRNA specificity is often assessed through gene expression profiling with microarrays, an approach that does not detect OTEs caused by altered translation. A second and more controversial possible cause of OTE is siRNA-mediated activation of the interferon pathway.

SUMMARY OF THE INVENTION

In accordance with the present invention, methods are provided for determining the specificity of RNA silencing in plants and other organisms. An exemplary method of the invention entails providing a cell exhibiting a silenced phenotype in which a target nucleic acid has been silenced by RNAi (either by siRNA supplied exogenously or produced in vivo from a transgene whose transcript is readily processed by the cell into an siRNA). A synthetic nucleic acid sequence is generated which encodes an identical protein to that encoded by the silenced target nucleic acid, (e.g., codon sequences in the synthetic nucleic acid construct are altered from the nucleic acid encoding the silenced target nucleic acid so as to reduce the nucleic acid sequence identity between the target and synthetic nucleic acid constructs). The synthetic nucleic acid construct is introduced into the cell exhibiting the silenced phenotype and ability of the synthetic construct to reverse the silenced phenotype is assessed. Reversal of the phenotype indicates that the siRNA is acting specifically on its target and maintenance of said silenced phenotype indicates that said siRNA is acting via an off-target mechanism.

Cells suitable for use in the method of the invention include any cell type where silencing is observed, e.g., plant cells, mammalian cells (including human cells), insect cells, yeast cells and cells from C. elegans. The synthetic nucleic acid construct can introduced into the cells via a variety of methods, including for example, transfection, transduction, agrobacterium-mediated infection, and biolistic particle delivery. In a preferred embodiment, the cell is a plant cell present in a plant.

In yet another aspect of the invention, methods are provided for performing functional analysis of the protein encoded by the synthetic nucleic acid construct in those cases where introduction of the synthetic construct reverses the silenced phenotype. Altering the coding sequence, by site-directed mutagenesis for example, enables the skilled person to assess the effects of different mutations or alterations on the ability of the encoded protein to modulate the silenced phenotype.

In another aspect of the invention, methods are provided for developing synthetic nucleic acid constructs useful for the treatment of genetic disorders related to the expression of mutated proteins (e.g., cystic fibrosis or Neiman-Pick Syndrome, sickle cell anemia or Tay Sachs). An exemplary method entails silencing the defective gene by siRNA followed by introduction and expression of a wild-type protein encoded by a synthetic nucleic acid construct which escapes RNA silencing. Such an approach should restore a functional protein, thereby alleviating the genetic defect.

The present invention also provides a kit for practicing the methods described above. An exemplary kit includes without limitation, a vector suitable for insertion of the synthetic nucleic acid sequence, reagents effective for introducing exogenous nucleic acids into cells, and optionally instructional material and culturing vessels or plates.

DETAILED DESCRIPTION OF THE INVENTION

Figure 1:
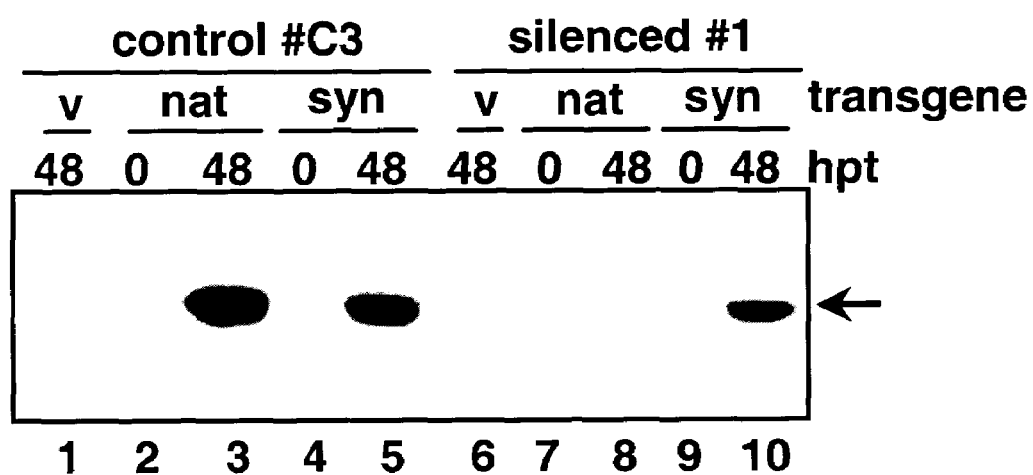
FIG. 1 shows immunoblot analysis of SABP2 expression in stably transformed vector control line #C3 and SABP2-silenced line #1(7), which were transformed with an estradiol-inducible native (nat) or synthetic (syn) salicylic acid-binding protein (SABP)2 gene, or with an empty pER8 vector (V). Leaf tissue was harvested at 0 and 48 hours after plants were treated with 30 μM estradiol.

To address the problem of confounding OTE effects, a method termed "syn gene complementation" or SGC, has been developed and experimentally validated to directly test the specificity of siRNA for its target. The method uses a synthetic (syn) gene encoding an identical protein to that of the targeted native (nat) gene but employs a different DNA/mRNA sequence specifically designed to escape RNAi silencing. If the phenotype induced by the siRNA is due to on-target silencing, it should be reversed by expression of the syn gene, whereas if it is due to OTE, expression of the syn gene will not fully suppress/reverse the phenotype. In the example described hereinbelow, it is demonstrated that expression of a syn, but not a nat, SABP2 gene restores systemic acquired resistance (SAR) to tobacco mosaic virus (TMV) in tobacco plants silenced for expression of the salicylic acid-binding protein (SABP)2 gene (7).

The methods of the present invention also facilitate performance of genetic analysis on those synthetic nucleic acid constructs which are effective in reversing the silenced phenotype. The synthetic nucleic acid can be altered or mutated by site-directed mutagenesis for example and its ability to modulate the silenced phenotype assessed.

The methods of the present invention also facilitate complementation of a genetic defect. This involves silencing the defective gene with siRNA and introducing and expressing a wild type protein encoded by a synthetic nucleic acid which is not subject to RNAi.

Table 1 below provides a list of important targets in human disease wherein RNAi has been observed either in humans (or in human cells) or for homologues of these gene in mice or *C. elegans* (9-14).

TABLE 1

| Human Disease | Human Gene |
|---|---|
| Macular degeneration | vascular endothelial growth factor (VEGF) |
| Hepatitis | Fas receptor |
| Acute liver failure | caspase 8 |
| Chronic myeloid leukemia | bcr/abl |
| Resistance to chemotherapy | MDR1 |

Table 2 below, taken from Shankar et al. (2005) JAMA 293:1367-73, as well as the two other examples provided hereinbelow, describe examples of RNAi therapeutic success in model rodents. In those cases where the disease is caused by a defective host gene (non-viral gene), the efficiency of treatment is likely to be enhanced by providing the corresponding non-defective protein using the synthetic gene complementation approach described herein.

TABLE 2

In Vivo Demonstrations of RNAi Therapeutic Efficacy in Rodents

| Tissue | Disease | Target Gene | RNAi Formulation | Delivery Route | Reference |
|---|---|---|---|---|---|
| Liver | AutoImmune Hepatitis | Fas | siRNA | Hydrodynamic (intravenous) | 26 |
| | Hepatitis B | HbsAg | siRNA | Hydrodynamic (intravenous) | 27, 28 |
| | Hepatitis B | Viral genes | shRNA from plasmid DNA | Hydrodynamic (intravenous) | 29 |
| | Hypercholesterolemia | apoB | Modified SIRNA coupled to cholesterol | Intravenous | 44 |
| CNS | Spinocerebellar ataxia-1 | Ataxin-1 | Adeno-associated viral vector | Intracerebellar | 30 |
| | Neuropathic pain | Cation channel | siRNA | Intrathecal | 31 |
| Eye | Neovascularization | VEGF | siRNA | Intraocular | 32 |
| Kidney | Acute tubular necrosis | Fas | siRNA | Renal vein or hydrodynamic | 33 |
| Lung | Influenza | Viral genes | siRNA complexed to polyethyleneimine | Intravenous | 34 |
| | | | shRNA expressed from plasmid DNA | Intranasal | 34 |
| | | | siRNA + siRNA-lipid complex | Hydrodynamic (intravenous) + intranasal | 35 |
| | Respiratory syncytial virus | Viral genes | siRNA with and without lipid | Intranasal | 36 |
| Tumors | Germ-cell tumor | FGF-4 | siRNA complexed to atelocollagen | Intratumoral | 37 |
| | Small-cell lung carcinoma | Skp-2 | Adenoviral vector | Intratumoral | 38 |
| | Pancreatic adenocarcinoma | CEACAM6 | siRNA | Hydrodynamic (intravenous) | 39 |
| | Glioblastoma | MMP-9 + cathepsin B | shRNA from plasmid DNA | Intratumoral | 40 |

Abbreviations: apoB, apolipoprotein B, CEACAM6, carcinoembryonic antigen-related cell adhesion molecule 6; CNS, central nervous system; FGF-4, fibroblast growth factor 4; HBsAg, hepatitis B surface antigen; MMP-9, matrix metalloproteinase 9; RNAi, RNA interference; shRNA, short hairpin RNA; siRNA, small interfering RNA; Skp-2, S phase kinase-associated protein; VEGF, vascular endothelial growth factor.

One of the causes of familial amyotrophic lateral sclerosis (ALS) leading to progressive death of motoneurons through a gain-of-function mechanism is mutations in Cu/Zn superoxide dismutase (encoded by SOD1). Using a mouse model it has been shown that RNAi-mediated silencing of the disease causing mutant SOD1 substantially retards both the onset and the progression rate of the disease (Raoul et al. (2005) Nat Med., 11:423-428; Ralph et al. (2005) Nat. Med., 11:429-433).

Another example is a dominant polyglutamine expansion diseases, including spinocerebellar ataxia type 1 (SCA1) and Huntington disease which are progressive, untreatable, neurodegenerative disorders. RNA interference (RNAi) has been used to inhibit polyglutamine-induced neurodegeneration caused by mutant ataxin-1 in a mouse model of SCA1 (Xia et al. (2004) Nat. Med., 10:816-20).

I. Definitions:

The following definitions are provided to facilitate an understanding of the present invention:

The term "pathogen-inoculated" refers to the inoculation of a plant with a pathogen.

The term "disease defense response" refers to a change in metabolism, biosynthetic activity or gene expression that enhances a plant's ability to suppress the replication and spread of a microbial pathogen (i.e., to resist the microbial pathogen). Agents that induce disease defense responses in plants include, but are not limited to: (1) microbial pathogens, such as fungi, oomycetes, bacteria and viruses; (2) microbial components and other defense response elicitors, such as proteins and protein fragments, small peptides, β-glucans, elicitins, harpins and oligosaccharides; and (3) secondary defense signaling molecules produced by the plant, such as SA, $H_2O_2$, ethylene and jasmonates.

The phrase "transgenic plant" refers to a plant whose genome has been altered by the introduction of at least one heterologous nucleic acid molecule.

The term "co-suppression" refers to a process whereby expression of a gene, which has been transformed into a cell or plant (transgene), causes silencing of the expression of endogenous genes that share sequence identity with the transgene. Silencing of the transgene also occurs.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$Tm=81.5°C.+16.6\,Log[Na+]+0.41(\%\,G+C)-0.63(\%\,formamide)-600/\#bp\,in\,duplex$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5× Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 μg/ml denatured salmon sperm DNA at 42° C., and washed in 0.1× SSC and 0.5% SDS at 65° C. for 15 minutes.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. A probe may be either single stranded or double stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non complementary nucleotide sequence may be attached to the 5' end of an otherwise complementary primer. Alternatively, non complementary bases may be interspersed within the oligonucleotide primer sequence, provided that the primer sequence has sufficient complementarity with the sequence of the desired template strand to functionally provide a template primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo or deoxyribonucleotides, preferably more than three. The exact size of the oligonucleotide will depend on various factors and on the particular application and use of the oligonucleotide.

The phrase "small, interfering RNA (siRNA)" refers to a short (typically less than 30 nucleotides long) double stranded RNA molecule. Typically, the siRNA modulates the expression of a gene to which the siRNA is targeted.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The phrase "operably linked", as used herein, may refer to a nucleic acid sequence placed into a functional relationship with another nucleic acid sequence. Examples of nucleic acid sequences that may be operably linked include, without limitation, promoters, transcription terminators, enhancers or activators and heterologous genes which when transcribed and, if appropriate to, translated will produce a functional product such as a protein, ribozyme or RNA molecule.

The phrase "off target effects" refers to an RNAi's influence on genes and proteins that it is not designed to target.

The phrase "silenced phenotype" as used herein refers to the alterations in phenotype (characteristic of the cell, tissue or organism) induced by an siRNA designed to silence a specific target gene or protein.

A "synthetic nucleic acid sequence" as used herein refers to a sequence which is different at the nucleic acid level than the target nucleic acid but encodes an identical amino acid sequence or protein.

A "mammalian cell" as used herein refers to any cell isolated from a mammal including humans.

An "insect cell" refers to cells isolated from insects, including without limitation, Drosophila cells or mosquito cells.

II. Methods and Kits for Practicing the Invention

The method of the invention can be used to advantage to ensure that siRNAs are acting in a sequence specific fashion to effect silencing of the target gene or protein. The method also provides the means to assess and further characterize those silencing mechanisms which are responsible for off-target effects.

The invention also provides a kit for practicing the method described herein. An exemplary kit includes a vector suitable for introducing a synthetic and/or native gene into a cell.

Reagents suitable for effectively introducing the vector into a cell and assessing the phenotype of the silenced nucleic acid may also be included. The kit may also contain instructional material to facilitate the practice of the method of the invention.

The invention also provides a means by which a gene or protein can be characterized through genetic analysis using mutated versions of a synthetic gene to complement the phenotype induced by RNAi-mediated silencing of that gene or protein. Such synthetic gene sequences can be assessed for their capacity to modulate the silenced phenotype.

The following example provides illustrative methods of practicing the present invention. It is not intended to limit the scope of the invention in any way.

EXAMPLE

Complementation of Systemic Acquired Resistance (SAR)-Defective Phenotype in SABP2-Silenced Tobacco A syn SABP2 gene that is 77% identical to nat SABP2, with nine nucleotides as the longest stretch of perfect identity, was synthesized by DNA 2.0, Inc (Menlo Park, Calif.). Codon substitution was used to maximize the difference in DNA sequence while retaining the codon preference for tobacco and avoiding DNA repeats, RNA secondary structures and putative splice sites (8). Control #C3 line and SABP2-silenced #1 line were then stably transformed with estradiol-inducible nat or syn SABP2 genes or the empty pER8 vector. Both nat and syn SABP2 were detected at similarly high levels in control #C3 plants, which carry an empty silencing vector (FIG. 1, lanes 3 and 5). In contrast, while substantial levels of syn SABP2 were detected in SABP2-silenced line #1 (lane 10), nat SABP2 expression was completely suppressed (FIG. 1, lane 8). Since the level of syn SABP2 in the silenced plants was lower than that in the control plants (compare lane 10 with 5), syn SABP2 was partially silenced; however, it was much higher than the endogenous SABP2 level in unsilenced plants (compare lane 10 with 1).

Figure 2:
FIG. 2 shows a series of photographs of leaves from the same stably transformed lines as in FIG. 1 at 6 days after secondary (2°) infection with TMV. Size of TMV lesions after primary (1°) or secondary (2°) infection with TMV (4 days post inoculation; (dpi)) are given in mm ±SD under each panel.
Figure 2:
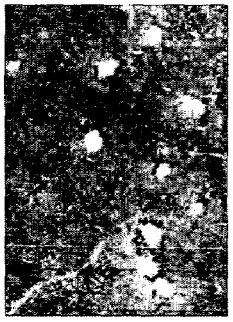
Figure 2:
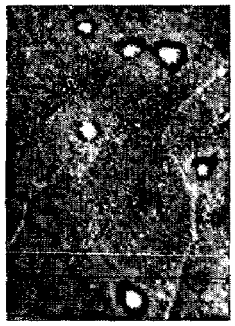
Figure 2:
Figure 3:
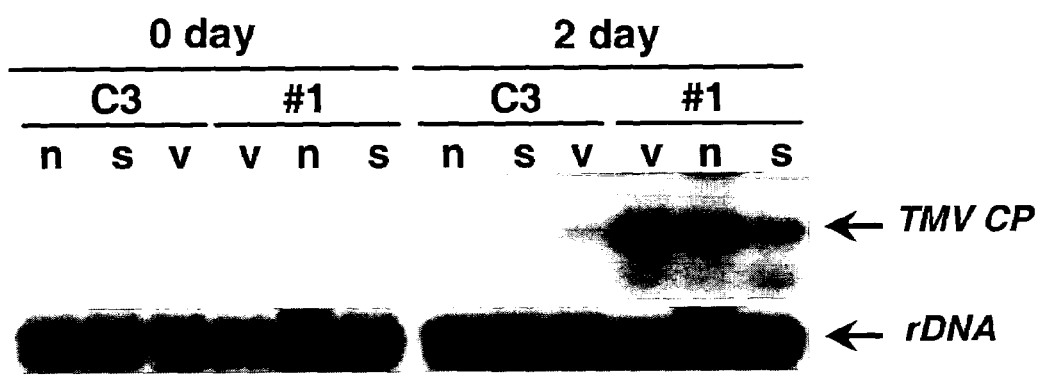
FIG. 3 shows northern blot analysis of TMV replication, based on the level of coat protein (CP) transcripts, in the 2° inoculated leaves of stably transformed control (C3) or SABP2-silenced #1 tobacco expressing an empty pER8 vector (v) or vector containing nat SABP2 (n) or syn SABP2 (s) at 0 and 2 dpi. About 40 hours post 1° inoculation, the uninoculated leaves were treated with 30 µM estradiol to induce SABP2 expression, and at 7 dpi these upper leaves were inoculated with TMV.

Whether this intermediate level of syn SABP2 expression restored SAR in SABP2-silenced plants was then tested. In control #C3 plants, lesions formed after secondary (2°) infection with TMV were ~50% smaller than those produced after a primary (1°) infection (FIG. 2); this reduction in 2° lesion size is a common indicator of SAR. In contrast, SABP2-silenced plants failed to develop SAR (7), as evidenced by the similar sizes of 1° and 2° lesions (FIG. 2) and the high level of TMV transcripts detected in their secondarily inoculated leaves (FIG. 3). This SAR-defective phenotype was not reversed by expression of nat SABP2 (FIG. 2); however, expression of syn SABP2 restored SAR, as indicated by suppression of both 2° lesion size (FIG. 2) and TMV replication (FIG. 3).

Figure 4:
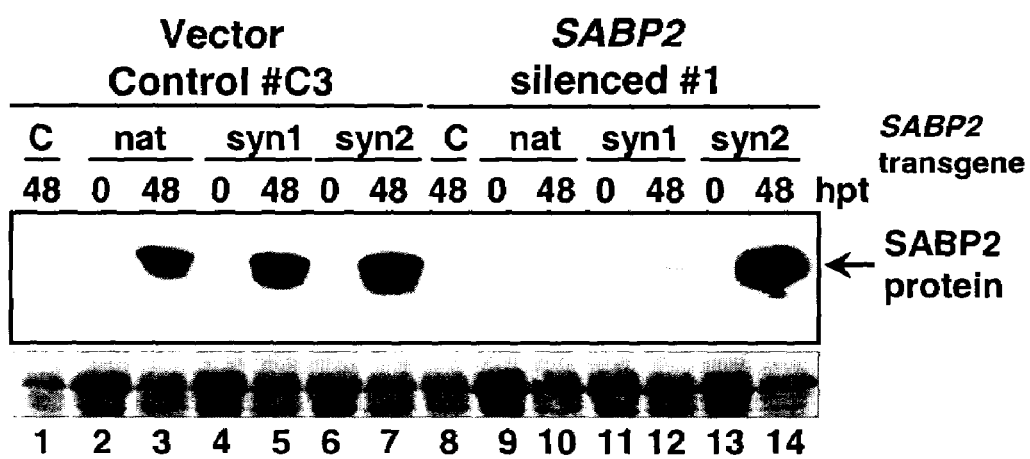
FIG. 4 is an immunoblot showing transient expression of native (nat) and synthetic SABP2 (syn1 and syn2) in control (#C3) and SABP2-silenced (#1) tobacco plants. 24 hours post inoculation (hpi) of SABP2-silenced tobacco #1 or of empty vector transformed control plants #C3 with Agrobacteria carrying the native (nat) or syn SABP2 (syn1 or syn2) gene under control of the estradiol-inducible XVE system, infected plants were treated with 30 µM estradiol and leaf tissue sampled immediately (0 hp treatment) or 48 hours later (48 hpt) for immunoblot analysis with antibodies against SABP2. A second control was tissue harvested 48 hpt with estradiol from plants infected with Agrobacteria not carrying an SABP2 transgene (V).

FIG. 4 shows that another synthetic DNA/gene (syn2) in which the similarity to native gene (used for RNAi construct) has been further reduced. SABP2 syn2 is only 61.8% similar to native SABP2 compared to SABP2 syn which is 77% similar/identical to native SABP2 at the nucleotide level. These data demonstrate that the synthetic gene sequence can be altered in a variety of ways.

Complementation of the SAR-defective phenotype in SABP2-silenced plants by expression of syn SABP2 argues that silencing of SABP2 alone is responsible for the SAR defective phenotype. It also indicates that our syn gene complementation approach will be a useful way to address OTE of siRNA in general. An advantage of this approach is that it assesses the phenotype resulting from RNAi and therefore is independent of the mechanism(s) for silencing the target gene or off-target gene(s). Moreover, this method provides the means to test not only possible off-target effects but also to perform genetic analysis of the target gene or protein through mutagenesis.

The method also provides the means to complement a genetic defect by silencing the defective gene by siRNA followed by expression of the wild type protein by a synthetic nucleic acid construct which is not subject to RNA silencing.

REFERENCES

1. J. Couzin, Science 306, 1124 (2004)
2. A. L. Jackson, P. S. Linsley, Trends Genet. 20, 521 (2004)
3. A. L. Jackson, et. al., Nat. Biotech. 21, 635 (2003)
4. S. Saxena, Z. O. Jonsson, A. Dutta, J. Biol. Chem. 278, 44312 (2003)
5. P. C. Scacheri et al., Proc. Natl. Acad. Sci. U.S.A. 101, 1892 (2004)
6. A. J. Bridge, S. Pebernard, A. Ducraux, A. L. Nicoulaz, R. Iggo, Nat. Genet. 34, 263 (2003)
7. D. Kumar, D. F. Klessig, Proc. Natl. Acad. Sci. U.S.A. 100, 16101 (2003)
8. C. Gustafsson, S. Govindarajan, J. Minshull, Trends Biotech. 22, 346 (2004)
9. R. S. Kamath et al. Nature 421, 231 (2003)
10. A. Adams The Scientist (March 29, 2004) 32-35
11. C. Raoul et al. Nature Medicine 11, 423 (2005)
12. H. Xia et al. Nature Medicine 10, 816 (2004)
13. G. Ralph et al. Nature Medicine 11, 429 (2005)
14. P. Shankar et al. JAMA 293, 1367 (2005)

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining whether a phenotype resulting from introduction of an siRNA into a cell is due to silencing of an intended target gene, or due to off-target effects, comprising:
   a) providing a cell exhibiting a silenced phenotype in which a target nucleic acid has been silenced by exogenously introduced siRNA, wherein said cell is selected from the group consisting of a plant cell, a yeast cell, an insect cell, or a cell from *C. elegans*;
   b) providing a synthetic nucleic acid sequence which encodes an identical protein to that encoded by the silenced target nucleic acid of step a), whereby codon sequences in said synthetic nucleic acid are altered from those of the silenced target nucleic acid so as to reduce the nucleic acid sequence identity between said target and synthetic nucleic acids;
   c) introducing the synthetic nucleic acid of step b) into the cell of step a) and assessing whether the silenced phenotype has been reversed indicating that said siRNA is acting specifically on its target or whether part or all of said silenced phenotype is maintained indicating that said siRNA is acting via an off-target mechanism.

2. The method of claim 1, wherein said cell is a plant cell.

3. The method of claim 1, wherein said phenotype is absence of systemic acquired resistance and said target nucleic acid encodes salicylic acid-binding protein 2.

4. The method of claim 3, wherein said synthetic nucleic acid sequence is 77% identical to the target nucleic acid sequence.

5. The method of claim 3, wherein said synthetic nucleic acid sequence is 61% identical to the target nucleic acid sequence.

6. The method of claim 1, wherein said synthetic nucleic acid is introduced into said cell via a method selected from the group consisting of electroporation, transfection, transduction, agrobacterium-mediated infection, and biolistic particle delivery.

7. The method of claim 1, wherein said cell is a plant cell present in a plant.

8. The method of claim 1, wherein said cell is selected from the group consisting of a yeast cell, an insect cell or a cell from *C. elegans* said cell optionally being present in said yeast, insect or *C. elegans*.

9. The method of claim 8, wherein said cell is from *C. elegans* and said synthetic construct is introduced into said cell by feeding said from *C. elegans* a bacterium expressing said synthetic construct.

10. The method of claim 1, wherein introduction of said synthetic nucleic acid construct fully reverses said silenced phenotype, said method comprising performing functional analysis of the protein encoded by said synthetic nucleic acid.

11. The method of claim 10, wherein following observation of full reversal of said silencing phenotype, said synthetic nucleic acid construct is further altered via site-directed mutagenesis to change the encoded amino acid sequence and introduced into said cell of part a) exhibiting silencing to assess the effects of said alterations on the silenced phenotype.

12. A method for determining whether a phenotype resulting from introduction of an siRNA into a mammalian cell is due to silencing of an intended target gene, or due to off-target effects, comprising:
  a) providing an isolated mammalian cell exhibiting a silenced phenotype in which a target nucleic acid has been silenced by exogenously introduced siRNA;
  b) providing a synthetic nucleic acid sequence which encodes an identical protein to that encoded by the silenced target nucleic acid of step a), whereby codon sequences in said synthetic nucleic acid are altered from those of the silenced target nucleic acid so as to reduce the nucleic acid sequence identity between said target and synthetic nucleic acids;
  c) introducing the synthetic nucleic acid of step b) into the cell of step a) and assessing whether the silenced phenotype has been reversed indicating that said siRNA is acting specifically on its target or whether part or all of said silenced phenotype is maintained indicating that said siRNA is acting via an off-target mechanism.

13. The method of claim 12, wherein introduction of said synthetic nucleic acid construct reverses said silenced phenotype, and then further altering said synthetic nucleic acid construct via site-directed mutagenesis to change the encoded amino acid sequence, and introducing it into said cell of part a) exhibiting silencing, to assess the effects of said alterations on the silenced phenotype.

\* \* \* \* \*

UNITED STATES PATENT AND TRADEMARK OFFICE
CERTIFICATE OF CORRECTION

PATENT NO. : 7,592,504 B2  Page 1 of 1
APPLICATION NO. : 11/452821
DATED : September 22, 2009
INVENTOR(S) : Klessig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 377 days.

Signed and Sealed this

Twenty-first Day of September, 2010

David J. Kappos
*Director of the United States Patent and Trademark Office*